United States Patent [19]
Von Bargen et al.

[11] 3,984,688
[45] Oct. 5, 1976

[54] MONITOR FOR DETECTION OF CHEMILUMINESCENT REACTIONS

[75] Inventors: John D. Von Bargen, Cypress; Khalid U. Siddiqui, Westminister, both of Calif.

[73] Assignee: Source Gas Analyzers, Inc., Garden Grove, Calif.

[22] Filed: Apr. 21, 1975

[21] Appl. No.: 569,706

[52] U.S. Cl. ............................. 250/361 C; 23/254 E
[51] Int. Cl.² ............................................ G01T 1/20
[58] Field of Search ............... 250/361 C; 23/232 E, 23/254 E

[56] References Cited
UNITED STATES PATENTS

| | | | |
|---|---|---|---|
| 3,710,107 | 1/1973 | Warren et al. | 250/361 C |
| 3,882,028 | 5/1975 | Zolner | 250/361 C |

*Primary Examiner*—Davis L. Willis
*Attorney, Agent, or Firm*—Frederick E. Mueller

[57] ABSTRACT

A monitor continuously senses light emitted by the chemiluminescent reaction of such substances as ozone and nitric oxide in order to measure an unknown quantity or concentration of one of the substances which may, for example, be an air pollutant. The monitor comprises a specially designed reaction chamber intended to utilize a high concentration reactant gas in such a fashion as to permit the measurement of light output of the chemiluminescent reaction with the sample gas by a solid state detector and associated electronics which eliminate the need for the use of a photomultiplier tube. The reactor body has an end closure means to form an annular plenum chamber surrounding a light transmitting means mounted by the closure means in one end of the reaction chamber. An annular discharge passage for discharging a conical curtain of reactant mixture from the plenum chamber axially into the reaction chamber around and away from the light transmitting means to prevent obscuration thereof by dirt from the sample is formed between the reactor body and the closure. The solid state detector is mounted outside the reaction chamber and adjacent to the light transmitting means.

13 Claims, 4 Drawing Figures

MONITOR FOR DETECTION OF CHEMILUMINESCENT REACTIONS

BACKGROUND OF THE INVENTION

Efforts to reduce and control the quantity of air pollutants in the atmosphere have resulted in the development of instrumentation for measuring air pollutants such as the oxides of nitrogen by measuring the light resulting from their chemiluminescent reaction with ozone. United States patents which are typical of such instruments include Nos. 3,528,779 to A. Fontijn; 3,692,485 to R. M. Neti et al; 3,700,896 to H. H. Anderson; 3,746,513 to A. Warnick et al; 3,746,514 to A. D. Colvin et al; 3,749,929 to G. W. Wooten; and 3,849,653 to R. R. Sakaide.

In these prior art devices it has been necessary either to use a large, fragile, and costly photomultiplier tube in combination with the chemiluminescent detection devices in order to measure the small amount of light from the reaction, or to abandon the chemiluminescent technique in order that the greater light output available from bioluminescent reactions may be used to permit the use of a low impedance solid state cadmium sulfide detector as, for example, in Sakaide. Neither of these alternatives is entirely satisfactory.

It is an object of the present invention to provide a device for the continuous detection of light emitted by the chemiluminescent reaction of ozone and nitric oxide which utilizes a high impedance solid state detector and associated electronics including a high gain current amplifier for greater overall detector sensitivity, in combination with a specifically designed reaction chamber to increase reaction light output sufficiently to permit the use of the more sensitive high impedance detector.

SUMMARY OF THE INVENTION

The device utilizes the phenomenon of chemiluminescence in which light is produced as a by-product of a chemical reaction. In a chemiluminescent reaction, the intensity of the light produced is proportional to the concentration of one gas if the concentration of the other gas is held constant. The chemiluminescent reaction of interest herein is that between nitric oxide (NO) and ozone ($O_3$) which is given by the expression

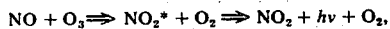

$$NO + O_3 \Rightarrow NO_2^* + O_2 \Rightarrow NO_2 + h\nu + O_2,$$

where $NO_2^*$ is the excited state of $NO_2$ and $h\nu$ is the light produced.

This reaction is utilized herein to measure the concentration of nitric oxide in a sample admitted to an elongated reaction chamber for reaction with ozone which is also supplied thereto. The reaction chamber is formed in a reactor body means having a separate closure member which sealingly closes one end thereof in such a fashion as to mount a light transmitting member such as a filter at an end of the chamber. The closure member supporting the light transmitting means also has formed in it an annular plenum chamber which surrounds the light transmitting means and coacts with the reactor body to form an annular outlet conduit surrounding the light transmitting means and inclined at an angle to both the filter and the axis of the reaction chamber so as to discharge a conically shaped curtain of reactant, e.g., high concentration ozone, into the reaction chamber in a direction away from the light filter and in a direction such that the apex of the conical flow falls substantially on the longitudinal axis of the chamber. The sample to be reacted with the ozone is directed into the reaction chamber at a point such that its flow will intersect with the apex of the conical flow. The effect of this arrangement is to supply a relatively high density (where by density is here meant molecules per unit volume) of ozone reactant at the reaction zone in a chamber which is operated overall at reduced pressure and also to preclude the collection of dirt from the sample on the surface of the light transmitting filter by flowing the sample away from the filter to an exhaust port at the opposite blind end of the chamber. The solid state detector is positioned adjacent to the light filter and electronic circuitry is provided to provide a measure of the light generated by the reaction as a measure of the concentration of the sample constituent in the reaction. The device thereby provides a lightweight, compact, rugged and efficient instrument for measuring chemiluminescent reactions.

BRIEF DESCRIPTION OF THE DRAWING

These and other objects, advantages, and features will become apparent from the detailed description below taken in conjunction with the accompanying drawings wherein like reference characters refer to like parts throughout and in which.

DETAILED DESCRIPTION OF THE INVENTION

Figure 1:
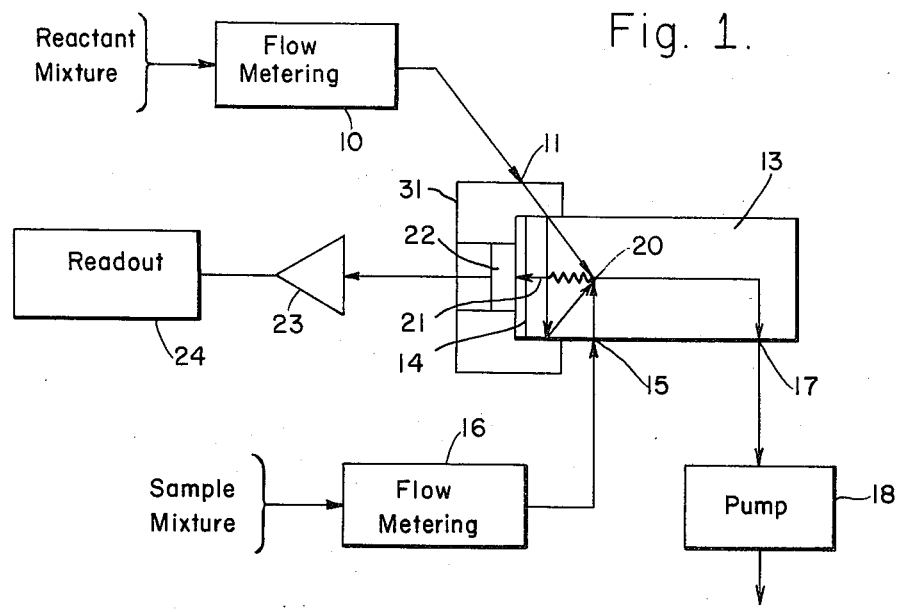
FIG. 1 is a block diagram of the overall system.

FIG. 1 is a block diagram of the system in which the monitor of the present invention is used. It will be seen that a reactant mixture is supplied through a conventional flow metering apparatus 10 to a reactant inlet 11 to a reaction chamber 13. As an NO monitor, the reactant mixture is here preferably a mixture containing between 2% and 6% ozone with dry oxygen as the carrier forming the balance of the flow. The reactant is introduced into the chamber 13 in a conical curtain flow pattern which is directed away from the filter or light transmitting means 14. The conical reactant flow, in the zone of its apex, merges with the sample mixture flow entering through an inlet 15 in the side of the reactor 13 from its flow metering system 16. The sample mixture contains an unknown concentration of nitric oxide to be measured. An exhaust conduit exit 17, at the opposite blind end of reactor 13 from the light transmitting element 14, is connected to a pump 18 which maintains the reaction chamber 13 at a reduced pressure which is preferably about 122 torr.

In operation the pump 18 is started to reduce the pressure in chamber 13 and the sample mixture and reactant mixtures are admitted through the flow metering devices to merge and react in the chamber in a small area concentrated around the apical zone 20. The chemiluminescent light output (indicated by the arrow 21) is transmitted through the light transmitting member 14 which seals the chamber 13 and thence into the solid state detector 22 which is positioned adjacent the outer surface of filter 14.

The light impinging on detector 22 has an intensity which for a given concentration and flow of ozone reactant mixture is proportional to the concentration of sample (here, nitric oxide) in the sample mixture. Also, the electrical output of the detector 22 is proportional to the intensity of light falling on it and is therefore also a measure of this concentration. This electrical output is supplied through an amplifier 23 to appropriate readout means 24 which provide to an operator a display of a measure of the concentration of pollutant in the sample.

Figure 2:
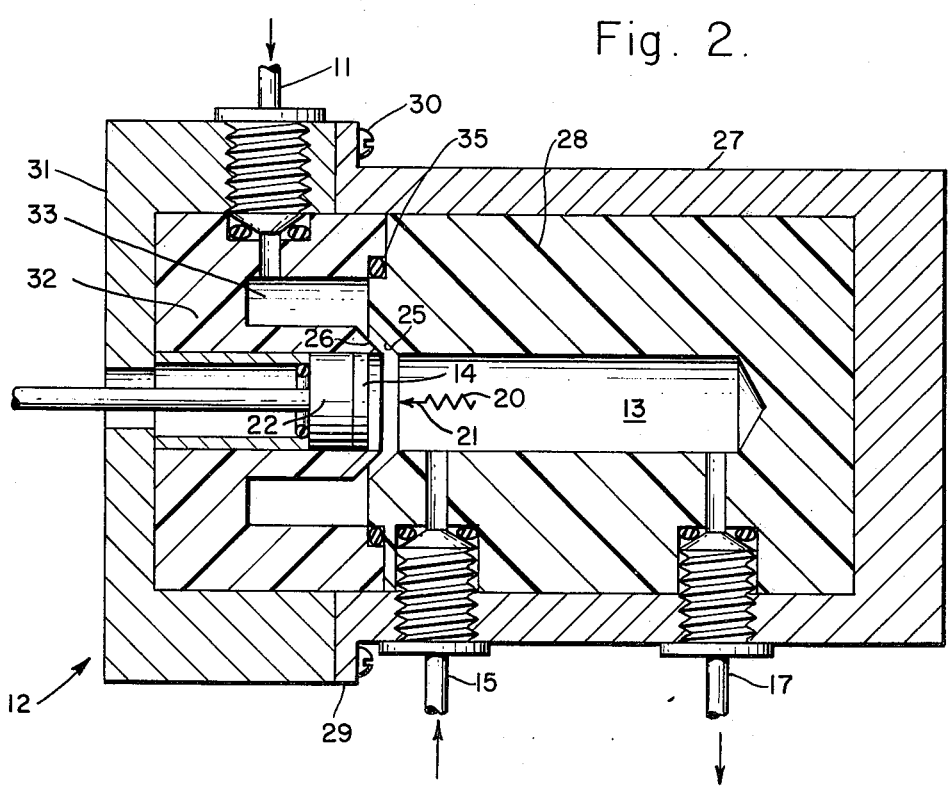
FIG. 2 is a sectional view of the reaction chamber assembly.
Figure 3:
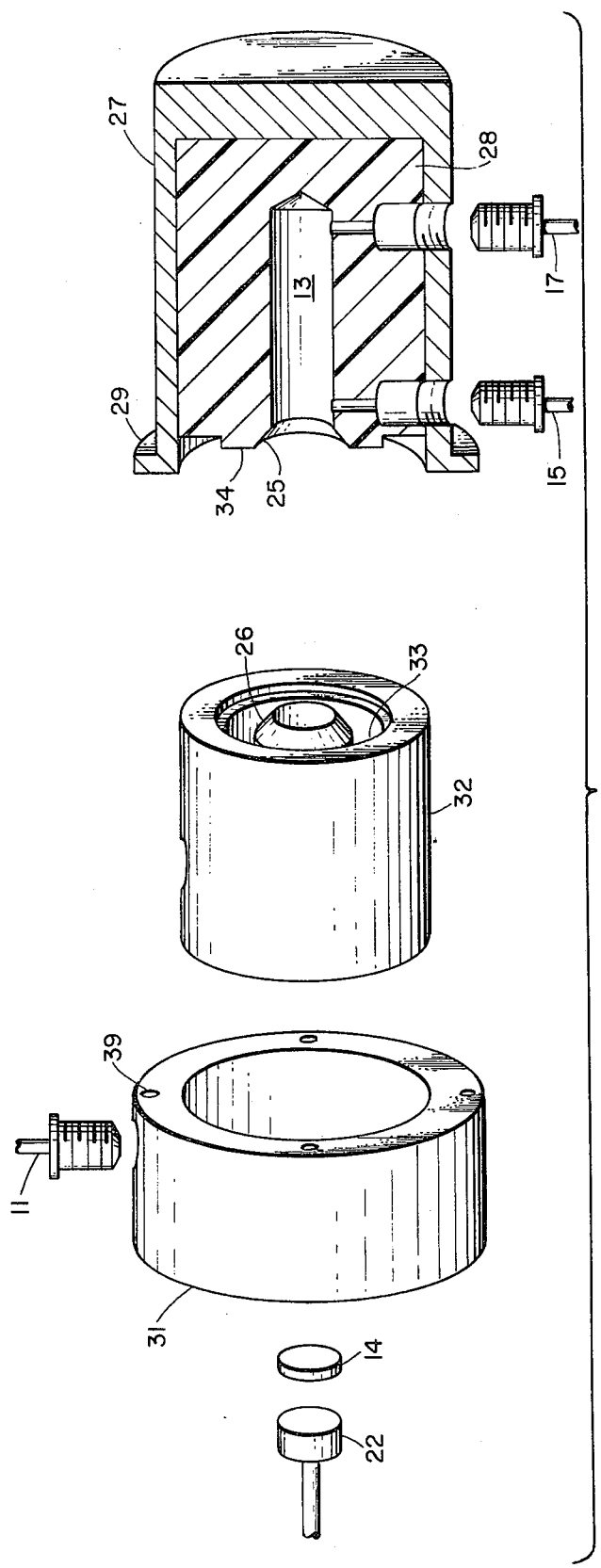
FIG. 3 is an exploded perspective view, partly sectioned, showing parts of the reaction chamber shown in FIG. 2.
Figure 4:
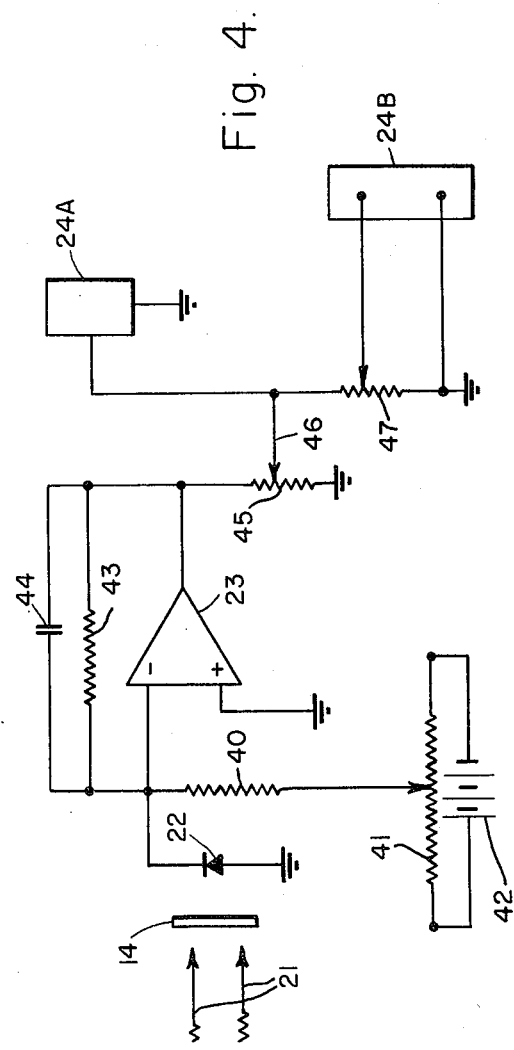
FIG. 4 is a circuit diagram of the electronics associated with the solid state detector and readout device.

FIGS. 2 and 3 show the physical structure of the reaction chamber. Ozone enters the reaction chamber 13 through an annular, axially frusto-conical orifice formed between the wall member 25 of reactor 13 and the wall member 26 of closure means 12. When assembled as shown in FIG. 2, the walls have a clearance of preferably about 1/100 of an inch between them. The nitric oxide sample enters the reaction chamber 13 from the side through conduit 15 and intersects the conical curtain flow of ozone at its apical zone 20 directly in front of filter 14 and detector 22. When the two gasses mix, the chemiluminescent reaction takes place and light is emitted in the direction of the arrow 21.

More specifically, the reactor assembly comprises an outer, hollow cylindrical housing 27, preferably of aluminum, in which an inner liner member 28 is inserted. The liner member 28 is composed of virgin teflon and is provided with a polished light reflecting central axial blind bore which forms the reaction chamber 13. Sample inlet conduit 15 is seated in a threaded opening drilled through housing 27 and liner 28 in the direction indicated above and the exhaust conduit 17 is similarly seated in a threaded opening drilled radially through the housing 27 and liner 28 into the blind end of the reaction chamber. The housing 27 is provided with an annular flange member 29 having holes provided therein to accomodate screws 30 by means of which the housing 27 may be fastened to closure member 31. Member 31 is also metallic and preferably aluminum and has screw receiving holes 39 therein to accomodate to screws 30, as well as a threaded aperture to accomodate the threaded inlet conduit 11. The inlet conduit 11 also extends through a virgin teflon insert 32 which, when assembled, is seated within the member 31, as seen in FIG. 2.

It will be noted from FIGS. 2 and 3 that the reactant mixture in the conduit 11 flows through member 31 and teflon liner 32 into an annular plenum chamber 33 having three of its sides defined by an annular recess cut into the teflon insert member 32. The surface 26 forming one wall of the annular discharge orifice leading from this plenum chamber 33 into the reaction chamber is a coaxial frusto-conical projection of the inner wall of the plenum chamber 33. This central portion is itself hollow and opens in the opposite direction from chamber 13 in order to provide a support area for the light transmitting filter 14 and the solid state detector 22 which are securely mounted therein by conventional means.

The other surface of the annular inlet orifice is formed by a bevelled surface 25 on the inlet end of teflon insert 28 carried in reactor housing 27. This surface 25 is continuous with the radial end surface 34 thereof which when assembled forms the fourth wall of the annular plenum chamber 33. The plenum chamber is sealed preferably by an O-ring 35 (FIG. 2 only) which is seated in a recess in insert member 28 and is sealed therein by the protrusion mating therewith from insert member 32.

The use of virgin teflon for the insert liner members 28 and 32 is prefered in order to eliminate the collection of film or coating contaminants that are inducted with the gasses to thereby increase the longevity of the light reflecting polished inner surface thereof forming reaction chamber 13 within which the reaction takes place. This permits the maximum efficiency in light collection for detection over an extended period of time.

Although there is not literally a point reaction at the intersection zone 20, the conical curtain does provide an increased density of molecules per cc. at this point. In plenum 33 the ozone is introduced at a high concentration of from 2% to 6% ozone in an oxygen carrier and thereby contributes to increased light output permitting the use of the lightweight solid state detector. Prior art devices use a concentration of about 1%. Furthermore, neither the ozone nor the sample have their flow directed against the glass light transmitting member 14 which thereby does not accumulate dirt during usage. The window is kept clean during use by directing the flow of ozone axially away from it via the orifice which concentrically surrounds it. By providing the exhaust conduit 17 at the blind end of the chamber 13 and by introducing the sample orthogonally to the chamber axis to the apex 20, the reaction occurs away from the window 14 and the gasses then are carried in the direction away from the window 14 to the exhaust conduit 17. Hence, the light collecting efficiency achieved by the use of the teflon liner is not impaired by fogging up the window 14.

Detector 22 may, for example, be a solid state silicon PIN detector such as that manufactured by United Detector Technology under their model number PAN-6DP. This detector 22, as best seen in FIG. 3, is connected in a circuit including an operational amplifier 23 which has the detector 22 connected between its negative input and ground. A bias resistor 40 is also connected from the negative input to a potentiometer resistor 41 which, in turn, is connected between the positive and negative terminals of a bias voltage supply 42 to form a zero control setting for the detector circuit. The positive input to amplifier 23 is grounded and a feed-back resistor 43 and a feed-back condensor 44 are connected from its output to the negative input in conventional fashion. A calibration control resistor 45 having a wiper arm pick off 46 is connected between the output of amplifier 23 and ground. The adjustment of the wiper arm 46 provides a calibration control for the readout circuit. The wiper arm 46 is connected both to a digital volt meter 24A and through a resistor 47 to ground. A recorder output may be taken from jacks 24B connected across the resistor 47.

It should be noted that the detector 22, one example of which was identified above as a United Detector Technology model PAN-6DP, is in any event preferably a PIN silicon photodiode. Cadmium sulphide photoresistor cells, although solid state photodetectors, have not been found suitable for use for detection of chemiluminescent reactions since the minimum light level to be detected is in the order of $2 \times 10^{-12}$ watts. The detection of such low light levels requires a sensitive detector and an extremely high current gain amplifier. To enable high current gain, the detector should have high source impedance. A cadmium sulphide cell has a low sensitivity and a low source impedance as compared to a silicon PIN photodiode. The PIN photodiode has a heavily doped "P" region and a heavily doped "N" region separated by a lightly doped "I" region. The "I" region provides the high impedance which is extremely desirable. In fact, the low source impedance of the detector is the limiting factor of the current gain that may be provided by the amplifier. The preferred detector identified above has a responsivity of 0.35 amps/wat, maximum light power density of 10 MW/CM$^2$ and an active area of 1.2 cm$^2$. The current output of the detector at the minimum light level is $10^{-14}$ amperes. The amplifier provides current gain of $10^{11}$. A varactor input operational amplifier is used for high input impedance and low drift. The source impedance of the silicon PIN photodiode used is about 40 megohms. The design of the reactor chamber 13, as discussed above, is such as to produce the necessary minimum light level of $2 \times 10^{-12}$ watts with the reactant concentration level and flow pattern specified.

The device as discussed above has been considered in its mode of operation as a means of measuring a variable or unknown concentration of nitric oxide by introduction of a constant known amount of ozone as a reactant. It will of course be understood that the device can also be used to monitor an unknown or variable amount of ozone if a constant known amount of nitric oxide is supplied and the device is appropriately calibrated. Other appropriately selected reactants and samples can of course also be used. In any mode it will be seen that we have provided a rugged, simple, lightweight and highly efficient chemiluminescent detector.

We claim:

1. In a monitor for determining the concentration of a gaseous constituent in a gaseous sample mixture by measuring the light output of a chemiluminescent reaction in a reaction chamber between the constituent and a gaseous reactant, the improvement comprising:
   a. means defining a reaction chamber having light transmitting means sealingly mounted in one end thereof;
   b. means for directing a flow of reactant gas into said reaction chamber adjacent to and in a direction avoiding said light transmitting means and through said reaction chamber;
   c. means to direct a flow of sample mixture into said reaction chamber along a path intersecting the reactant flow;
   d. means to exhaust gasses from said chamber proximate to the end remote from said light transmitting means; and
   e. light detector means positioned outside of said reaction chamber and adjacent to said light transmitting means for measuring the light transmitting through said light transmitting means from the chemiluminescent reaction in said reaction chamber between said constituent in the sample mixture and the reactant gas.

2. A monitor as in claim 1 wherein said means for directing the flow of reactant gas comprises a circular convergent orifice surrounding said light transmitting means to flow the reactant gas therethrough in a conical curtain having an apical zone in said chamber, said means for directing the flow of sample mixture being oriented for intersecting the apical zone of the reactant gas.

3. A monitor as in claim 1 wherein said light detector means is a silicon PIN photodiode having a high source impedance and having its output supplied through a high current gain amplifier to readout display means.

4. A monitor as in claim 1 wherein said reactor chamber means comprises a rigid cylindrical outer housing and a hollow cylindrical teflon insert mounted therein, the inner surface of said teflon insert defining said reaction chamber and being polished to augment light reflectivity.

5. In a monitor for determining the concentration of a gaseous constituent in a gaseous sample mixture by measuring the light output of a chemiluminescent reaction in a reaction chamber between the constituent and a gaseous reactant, the improvement comprising:
   a. reactor chamber means having a teflon liner inserted therein for defining a reaction chamber open at one end thereof;
   b. closure means sealingly closing said one end of said chamber and for mounting a light transmitting means in said end, said closure means and said teflon insert in said reactor coacting to form an annular plenum chamber surrounding said light transmitting means and an annular gas discharge means communicating said plenum chamber with said reaction chamber for directing a flow of reactant gas from said plenum chamber into said reaction chamber in a conical curtain surrounding said light transmitting means and having its apex directed into said reaction chamber and away from said light transmitting means;
   c. means to direct a flow of sample mixture into said reaction chamber along a line parallel to and spaced from said light transmitting means and intersecting the apex of said conical curtain flow;
   d. means to exhaust gasses from said chamber proximate to the end remote from said light transmitting means; and
   e. solid state light detector means positioned outside of said reaction chamber and adjacent to said light transmitting means for measuring the light transmitted through said light transmitting means from the chemiluminescent reaction at said apex of said conical curtain in said reaction chamber between said constituent in the sample mixture and said reactant gas.

6. A detector as in claim 5 wherein said closure means comprises a rigid outer housing and a teflon liner insert.

7. A detector as in claim 5 wherein said solid state light detector means is a silicon PIN photodiode having a high source impedance and having its output supplied through a high current gain amplifier to readout display means.

8. A chemiluminescent reaction detector for determining the concentration of a gaseous constituent in a gaseous sample mixture by measuring the light output of a chemiluminescent reaction between the constituent and a gaseous reactant, said reaction detector comprising:
   a. means forming an elongate reaction chamber having an exhaust conduit exit proximate to one otherwise closed end thereof and a central opening at the other end thereof;
   b. closure means for coacting with said chamber means to sealingly close said opening and to mount a light transmitting means in said opening orthogonally to the longitudinal axis of said chamber, said closure means and said chamber means also coacting to form an annular plenum surrounding said light transmitting means and an annular gas discharge means for directing a flow of gas from said plenum chamber into said reaction chamber;
c. said gas discharge means being shaped to direct said flow gas in a convergent conical curtain directed longitudinally into said reaction chamber and away from said light transmitting means, the apex of said conical curtain being on said longitudinal axis of said reaction chamber and spaced from said light transmitting means to minimize the contact of reactants with said light transmitting means;
d. means for evacuating gasses from said chamber through said exhaust conduit exit;
e. reactant conduit means connected to said plenum for admitting a high concentration gaseous reactant through said plenum and said annular discharge means into said reaction chamber; and
f. sample conduit means connected to said reaction chamber for directing said gaseous sample mixture into said reaction chamber along a line which intersects said longitudinal axis of said reaction chamber at said apex to meet the flow of said reactant gas at said apex of said conical curtain.

9. A detector as in claim 8 having light detector means positioned outside of said reaction chamber and adjacent to said light transmitting means for measuring the light transmitted through said light transmitting means from the chemiluminescent reaction at said apex of said conical curtain in said reaction chamber between said constituent in the sample mixture and said reactant.

10. A detector as in claim 9 wherein said light detector means is a silicon PIN photodiode having a high source impedance and wherein the output of said photodiode is supplied through a high gain current amplifier to current actuated readout means.

11. A detector as in claim 8 wherein said means forming said reaction chamber comprises a substantially cylindrical rigid outer housing having a chamber forming insert, said insert being composed of virgin teflon having a central polished bore defining said chamber and providing high light reflectivity therein.

12. A detector as in claim 11 wherein said closure means for coacting with said reactor chamber means comprises a rigid outer cylindrical housing having a virgin teflon insert member in which said light transmitting means is mounted and in which said annular plenum is formed for closure by coaction with said reactor insert.

13. In a monitor for determining the concentration of a gaseous constituent in a gaseous sample mixture by measuring the light output of a chemiluminescent reaction in a reaction chamber between the constituent and a gaseous reactant, the improvement comprising:
a. means defining a reaction chamber having light transmitting means sealingly mounted in one end thereof;
b. means for directing a flow of reactant gas into said chamber adjacent to and in a direction avoiding intersecting said light transmitting means;
c. means to direct a flow of sample mixture to said reaction chamber along a path intersecting the reactant flow;
d. means to exhaust gasses from said chamber proximate to the end remote from said light transmitting means; and
e. solid state light detector means positioned outside of said reaction chamber and adjacent to said light transmitting means for measuring the light transmitted through said light transmitting means from the chemiluminescent reaction in said reaction chamber between said constituent in the sample mixture and the reactant gas.

* * * * *